United States Patent [19]

Inoue et al.

[11] Patent Number: 4,944,178
[45] Date of Patent: Jul. 31, 1990

[54] APPARATUS AND METHOD FOR MEASURING DISSOLVED GAS IN OIL

[75] Inventors: Yasuo Inoue; Masanari Kikkawa; Masaru Kamba; Hiroshi Okuda, all of Kyoto, Japan

[73] Assignee: Nissin Electric Co., Ltd, Kyoto, Japan

[21] Appl. No.: 333,401

[22] Filed: Apr. 5, 1989

[30] Foreign Application Priority Data

| Apr. 18, 1988 | [JP] | Japan | 63-95238 |
| Sep. 27, 1988 | [JP] | Japan | 63-243709 |
| Sep. 27, 1988 | [JP] | Japan | 63-126807[U] |
| Sep. 27, 1988 | [JP] | Japan | 63-126809[U] |

[51] Int. Cl.⁵ .............................................. G01N 7/00
[52] U.S. Cl. ..................................................... 73/19.1
[58] Field of Search .................... 73/23, 19, 61.1 R; 55/270, 196

[56] References Cited

U.S. PATENT DOCUMENTS

| 2,987,912 | 6/1961 | Jacobson | 73/53 |
| 3,740,320 | 6/1973 | Arthur | 73/19 |
| 3,942,792 | 3/1976 | Topol | 73/19 |
| 4,330,385 | 5/1982 | Arthur | 73/23 |
| 4,546,640 | 10/1985 | Stone et al. | 73/19 |
| 4,681,601 | 7/1987 | Foster | 73/19 |
| 4,752,383 | 6/1988 | McKay et al. | 210/221.2 |
| 4,764,344 | 8/1988 | Knab | 73/19 |

Primary Examiner—Hezron E. Williams
Attorney, Agent, or Firm—Finnegan, Henderson, Farabow, Garrett & Dunner

[57] ABSTRACT

Apparatus and method for measuring a dissolved gas in oil wherein air is blown into an oil sample through a bubble generator, bubbles are passed through the oil sample to extract dissolved gas therefrom, a resulting air-extracted gas mixture is contacted by a gas sensor for detecting and measuring the dissolved gas and the mixture is recirculated through the oil sample. Preferably, the air bubbles are within the range of 0.1 mm to 8.0 mm, and, also, the volume of the apparatus is selected so that the quantity of the gas to be measured is not more than 20% of the combined volume of the extraction vessel, the sensor chamber, and the connecting conduit.

7 Claims, 5 Drawing Sheets

APPARATUS AND METHOD FOR MEASURING DISSOLVED GAS IN OIL

FIELD OF THE INVENTION

The present invention relates to a method and apparatus for measuring dissolved gas in oil.

BACKGROUND OF THE INVENTION

Conventionally, in order to measure a gas dissolved in oil, the following methods have been used.

In a first method, an oil sample is taken at a site, placed in a closed vessel and taken to an analysis room where an analyzing apparatus is provided. In the analysis room, a sample of oil from the vessel is put into an analyzer which extracts dissolved gas from the oil sample, and analyzes the extracted gas using a gas chromatograph to measure the kind and quantity of the dissolved gas.

In a second method, a permeable membrane flange is connected to an oil take-out valve on oil handling equipment, and a gas chamber is provided on the outside of the permeable membrane flange so that gas in oil passing through the permeable membrane is detected and the kind and quantity of the dissolved gas in the oil is measured.

In the first conventional method, there has been a problem in that it takes a long time from collecting the oil to analysis, so that the measurement of the gas is delayed, and the gas sometimes comes out of solution during transportation, thereby lowering the reliability of data. Further, the analyzing apparatus is expensive, and the analyzing operation is complicated and requires a skilled operator.

In the second method, on the other hand, there has been a problem in that the gas transmission time is three days or more, so that rapid evaluation cannot be performed. Also, it is necessary to provide a permeable membrane flange and a gas chamber for the oil handling equipment, so that the manufacturing cost of the equipment becomes high.

It is therefore an object of the present invention to provide a method and apparatus for measuring dissolved gas in oil with a simple arrangement in a short time.

SUMMARY OF THE INVENTION

The apparatus for measuring dissolved gas in oil, according to the present invention, comprises: an extraction vessel for containing an oil sample; a circulating pump for blowing air into the oil sample; a bubble generator for generating bubbles in the oil sample with the air blown by the pump to extract, or strip, dissolved gas from the oil sample; a measuring instrument for measuring the concentration of the extracted gas contained in the bubbles; and means for returning the air to the pump after measurement by the measuring instrument so that the air is blown again into the oil sample by the pump.

In order to measure gas dissolved in oil, a stripping gas such as air or the like, is passed, in the form of bubbles, through an oil sample taken from oil handling equipment so that dissolved gas in the oil sample is extracted from the oil and is entrained into the bubbles, and the gas extracted from the bubbles is collected and measured. Particularly, the apparatus employs a circulation system which is arranged so that air blown into the oil sample is returned into the vessel of the oil sample after it has been blown through the oil sample. As the result of using the foregoing circulation system, it is not necessary to provide a vent system. Therefore the apparatus can be lowered in cost and can be reduced in size. Further, the use of the foregoing circulation system makes it possible to shorten the measurement time, that is, the time taken before the measured value has become stable. Since the recovered gas extracted by stripping is circulated in the system, a vapor-liquid equilibrium state can be reached in a short time in the extraction vessel. The concentration in this vapor-liquid equilibrium state is the concentration of the dissolved gas per se, and therefore the gas concentration can be detected in a relatively short time.

According to another aspect of the present invention, the method of measuring a dissolved gas in oil comprises the steps of: passing a stripping gas such as air into a sample of oil contained in an extraction vessel, so as to form bubbles therein and to strip dissolved gas from the oil sample with the bubbles; recovering the gas extracted from the bubbles so as to measure the dissolved gas; and returning the recovered gas into the extraction vessel through a pump to thereby circulate the recovered gas.

DETAILED DESCRIPTION OF PREFERRED EMBODIMENTS

Figure 1:
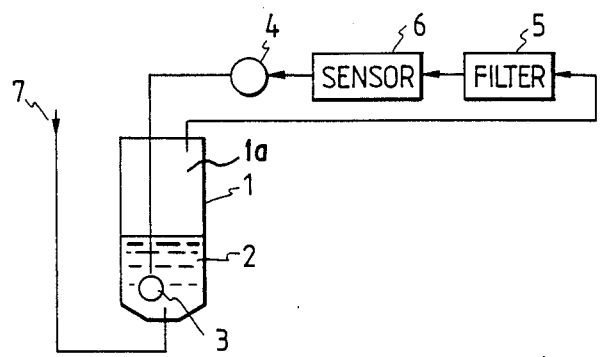
FIG. 1 is a diagram showing the arrangement of a first embodiment of the present invention.
Figure 2:
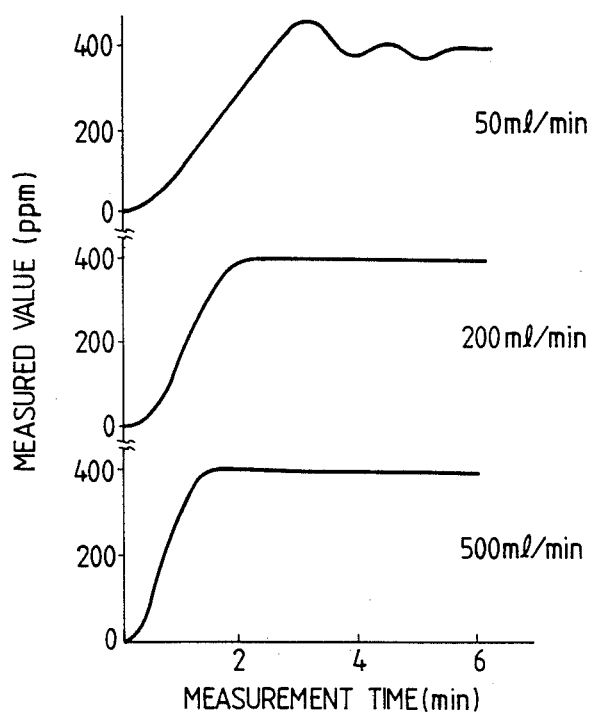
FIG. 2 is a diagram of a result of a characteristic experiment showing the indicated values of gas concentration with respect to the measuring time in the first embodiment.

Referring to FIGS. 1 and 2, a first embodiment of the present invention will be described hereinbelow. A closable extraction vessel 1 is provided for accommodating an oil sample 2 taken out of oil handling equipment. A bubble generator 3 constituted by a ball filter or a pipe alone is disposed in extraction vessel 1 below the level of the oil sample which only partially fills the vessel. External air to be used for bubbling is introduced into the bubble generator 3 through a pump 4.

Bubbles are generated with the air and pass upwardly through the oil sample to strip gas dissolved in the oil sample 2 from the oil. The bubbles contain a mixture of air and dissolved gas. The bubbles containing entrained gas disappear as they reach the upper portion 1a of the extraction vessel 1 which is not occupied by the oil. The resulting mixture of recovered dissolved gas and air which had formed the bubbles is then sent to a sensor 6, through a filter 5, which detects the gas mixed with the air. The detected value is converted, for example, into an electric signal, and indicated by a suitable indicator.

An injection inlet 7 is formed for injecting the oil sample 2 into the extraction vessel 1.

According to the present invention, the mixture of air and gas after being passed through the sensor 6 is sent again to the bubble generator 3 through the pump 4 and bubbled through the oil sample 2.

Examples of the dissolved gas in oil to be measured may include individual gas components including flammable gases, for example, $H_2$, methane, ethylene, acetylene, CO, $CO_2$, and the like. Therefore, an appropriate sensor, which may be of the conventional type, corresponding to the dissolved gas to be measured should be selected. In the case where hydrogen gas is to be measured, for example, a sensor composed of $SnO_2$ and responsive only to hydrogen passed through an $SiO_2$ membrane may be used. Further, a semiconductor sensor composed of metal oxide such as ZnO or the like may be used, depending on the kind of the dissolved gas to be measured. Preferably, the filter 5 is selected to have a pore size of about 0.2 μm.

Measurement using the apparatus of FIG. 1 is carried out in the following manner. First, oil sample 2 is injected from the injection inlet 7 into the extraction vessel 1, for example, about 20 ml by using an injector of the conventional type. The upper portion of the vessel is not occupied by the oil 2, since the vessel is only partially filled with the oil. The pump 4 is driven so as to circulate air through the extraction vessel 1 and connecting pipes. As a result, bubbles are generated in the oil 2 by the bubble generator 3, pass upwardly through the oil and rise to the surface of the oil sample 2. When the bubbles rise into the open space 1a, the bubbles disappear and the air and gas from the oil are recycled again into the extraction vessel 1 through the pump 4.

If a gas is dissolved in the oil sample 2, the gas is entrained into the bubbles, and the concentration of the gas is measured by the sensor 6. The recirculation of the air-gas mixture is continued until such time as the measured value becomes fixed, and the measurement is then completed. The indicated value of measurement at this time is the concentration of the gas in the oil sample.

FIG. 2 shows results of an experiment which has been made by the present inventor. In this experiment, an extraction vessel 1 having a volume which added up to 240 ml together with the volume of connecting piping was used. The quantity of an oil sample was set to 40 ml, and the flow rate of air blown by the pump 4 was changed to be 50 ml/min, 200 ml/min and 500 ml/min. Further, in this experiment, hydrogen was added to the oil sample in the concentration of 400 ppm.

As seen from FIG. 2, when the flow rate is low, for example, 50 ml/min, it took a relatively long time, for example, 5 minutes or more, before the concentration of the extracted gas became constant. This probably was because the air and extracted gas formed a laminar flow pattern in the oil in the extraction vessel 1 and the hydrogen was not quickly stripped from the oil. It can be therefore said that a flow rate of less then 100 ml/min is not desirable.

On the other hand, it was found that it takes about 2 minutes, and about 1.5 minutes, before the concentration of the extracted gas became constant when the flow rate was 200 ml/min and 500 ml/min, respectively.

The volume of the extraction vessel 1 and other portions of the system and the volume of oil sample 2 are important factors in measuring concentration. It is necessary to determine those volumes on the basis of how readily the oil defoams and the sensitivity of the sensor 6. Specifically, it is preferable to select the ratio of the volume of the open space 1a to the volume of oil sample to be within a range of from about 1 to about 20. As described above, according to the present invention, there is an excellent effect in that the concentration of a dissolved gas in oil can be measured with a simple arrangement in a short time relative to that of a conventional system.

A second embodiment of the present invention, as described hereinbelow provides certain advantages over the first embodiment, giving attention to the following characteristics of the first embodiment.

That is, in the first embodiment, since fine bubbles are used, it is necessary to provide a defoaming means, such as open space 1a for breaking the bubbles inside of the extraction vessel.

Further, since a predetermined volume of gas is required to be recovered, it is desirable to select the volume of open space 1a to be, for example, five times or more as large as the volume of the oil sample. If the volume of the open space 1a is selected to be five times as large as the volume of the oil sample, a value five times as large as the value indicated by the measuring instrument is a true one. Therefore, the sensitivity of the measuring instrument cannot be used as it is, so that the lower limit of concentration to be measured becomes, inevitably, a relatively large value, for example, 500 ppm.

The second embodiment of the present invention extends the range of measurement to low concentrations and makes it unnecessary to provide the defoaming means of the first embodiment.

In the technique of the present invention in which a gas contained in a recovered gas after extraction by bubbling is measured by a gas sensor and the gas after the measurement is returned again to an extraction vessel so as to circulate the recovered gas, an important feature of this second embodiment resides in selecting the size of the bubbles passed through to oil sample to be within the range of from 0.1 mm to 8.0 mm diameter.

Further, because the size of bubbles is made relatively large, to the extent that no measurement error is generated, the defoaming means becomes unnecessary and measurement of low concentrations of dissolved gas becomes possible.

Figure 3:
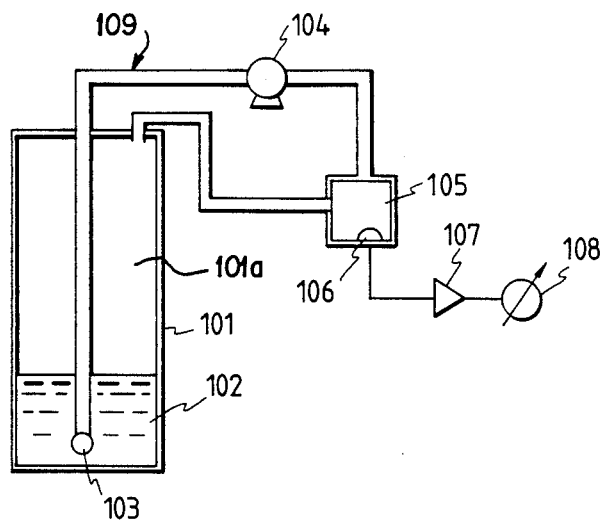
FIG. 3 is a diagram showing the arrangement of second and third embodiments of the present invention.

Referring to FIGS. 3 through 6, the second embodiment of the present invention will be described in more detail. FIG. 3 shows an apparatus of this embodiment which is substantially the same as that of FIG. 1. In the drawing, an oil sample 102 is contained in an extraction vessel 101. A bubble generator 103 constituted by a ball filter, a bubble generation pipe, or the like, is provided in the inside of the extraction vessel 101 near the bottom thereof. In measurement, the extraction vessel 101 is closed and a bubbling gas, for example, air or the like, is passed from the outside into the bubble generator 103 through a pump 104.

Bubbles are generated with the air. The bubbles contain air and dissolved gas stripped from the oil sample 102. The mixture of gases extracted from the bubbles is sent to a gas recovering vessel 105 so the dissolved gas is detected by a gas sensor 106 in the vessel 105. The detected value is converted into an electric signal, and amplified by an amplifier 107. The detected quantity is indicated by a meter 108. A suitable semiconductor sensor composed of metal oxide such as $SnO_2$, $ZnO$, or the like, sensitive to the gas to be measured is used as the gas sensor.

The mixture of air and extracted gas in the gas recovering vessel 105 is returned to the extraction vessel 101 by a pump 104 through a pipe 109. Thus, the air and extracted gas is repeatedly circulated, and the gas concentration is measured midway in the circulation system.

Figure 4:
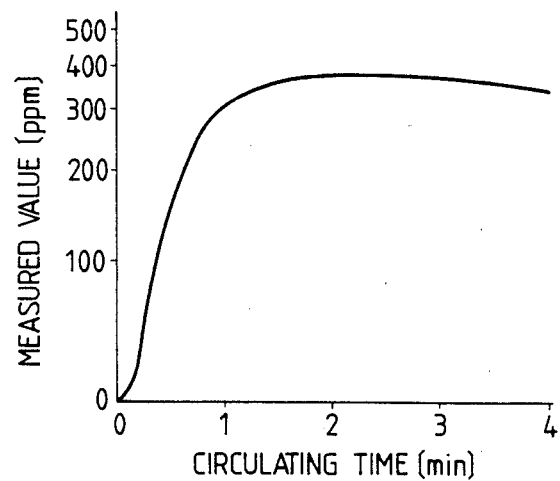
FIG. 4 is a diagram showing a gas concentration equilibrium curve in the second embodiment.

FIG. 4 shows an of a gas concentration equilibrium curve obtained by plotting an indicated value with respect to the circulating time, that is, by plotting an indicated value of the meter 108 as the time elapses after initiation of circulation, as a result of measurement of a hydrogen gas in oil by means of the semiconductor sensor of the apparatus of FIG. 3.

The peak of the curve shows that vapor-liquid equilibrium is reached, and at this point. The measurement is completed. In this example, the indicated value reached a peak (340 ppm) after a lapse of time of 1 minute and 40 seconds from the initiation of circulation.

Figure 5:
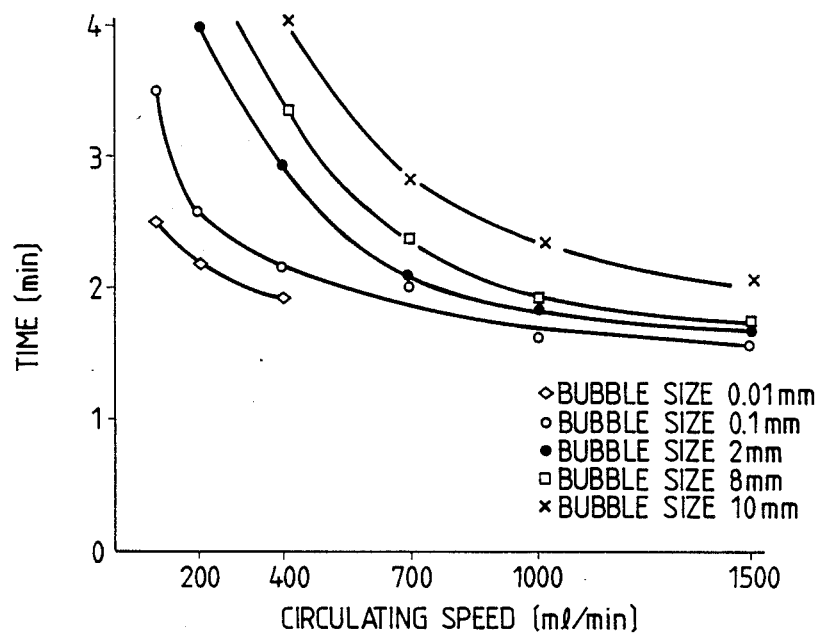
FIG. 5 is a diagram showing a vapor-liquid equilibrium time characteristic in the second embodiment.

FIG. 5 shows vapor-liquid equilibrium time characteristic curves obtained by detecting the time taken before the vapor-liquid equilibrium was reached with bubbles of varying sizes at varying flow rates of circulation. From these characteristic curves, it can be seen that the smaller the size of the bubbles and the higher the flow rate, the shorter the time required before the peak value was reached. It is therefore seen that the time for measurement can be shortened if the size of bubbles is decreased.

Figure 6:
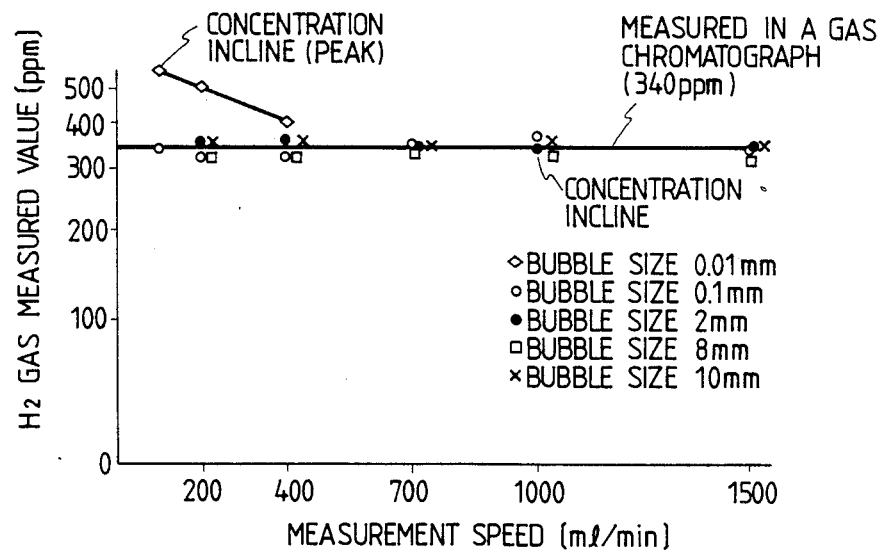
FIG. 6 is a diagram showing a concentration difference characteristic in the second embodiment.

As a result of examining the difference between the peak value and actual concentration of the dissolved gas, however, it was found that the result shown in FIG. 6 was obtained. That is, from the diagram, it is found that when the size of bubbles is small, the measured peak value obtained as an indicated value of the gas sensor 106 in the gas recovering vessel 105 indicated a value which was higher than the actual concentration. The concentration of the gas used in this case was 340 ppm when it was accurately measured in advance by means of a gas chromatograph.

From the result, it was found that if the size of bubbles is smaller than 0.01 mm, the peak value is not the true gas concentration even if the peak value was reached. Therefore, it is not desirable to use bubbles having a size less than 0.01 mm.

Even in the case where the size of bubbles is smaller than 0.1 mm, bubbles sometimes reach the gas recovering vessel 105 if they do not break in the extraction vessel 101, so that entrained oil touches the gas sensor 106 to thereby damage the sensor when the flow rate becomes high. It is therefore not desirable to use bubbles having a size smaller than 0.1 mm.

If the size of bubbles exceeds 8.0 mm, on the other hand, the time for measurement is so prolonged, as seen from FIG. 6, that such bubbles are unsuitable from the practical standpoint for the measurement of this kind.

If, however, the size of bubbles falls within a range of from 0.1 mm to 8.0 mm, bubbles spontaneously break, or disappear, in the extraction vessel 101. Therefore, it is not necessary to provide the defoaming means in the extraction vessel 101. In practice, the ratio of the volume of the oil sample to the volume of the open space 101a can be selected to be within a range of from 1:1 to 1:15. If the ratio is selected to be 1:1, measurement can be performed to the lowest limit of the sensitivity of the gas sensor, for example, 10 ppm, thereby making it possible to perform low concentration measurement.

As described above, this second embodiment has an excellent effect in that not only can a gas dissolved in oil be measured in short time, but the measurement can be made over a wide range of concentrations and the defoaming means it not necessary.

Next, a third embodiment of the present invention will be described. The third embodiment has been developed in view of the following problem in semiconductor gas sensors. That is, a semiconductor gas sensor characteristically consumes a gas to be detected during measurement. In measurement, therefore, the concentration of the gas varies, so that measurement errors are sometimes caused. The third embodiment of the present invention improves the accuracy in measurement of a dissolved gas in an oil sample.

The feature of this third embodiment is in that the volume of the measurement system is established so that such consumption of the gas to be measured by the gas sensor is not more than 20% in the period of time required for the gas extraction.

If the volume of the measurement system is established so that the consumption of a gas to be measured by the gas sensor is not more than 20% in the period of time required for the gas extraction when a dissolved gas is extracted by bubbling, recovered and measured while being circulated, the rate of concentration retention of the gas to be measured can be guaranteed so as to be not smaller than 80% to thereby improve the accuracy in measurement.

Figure 7:
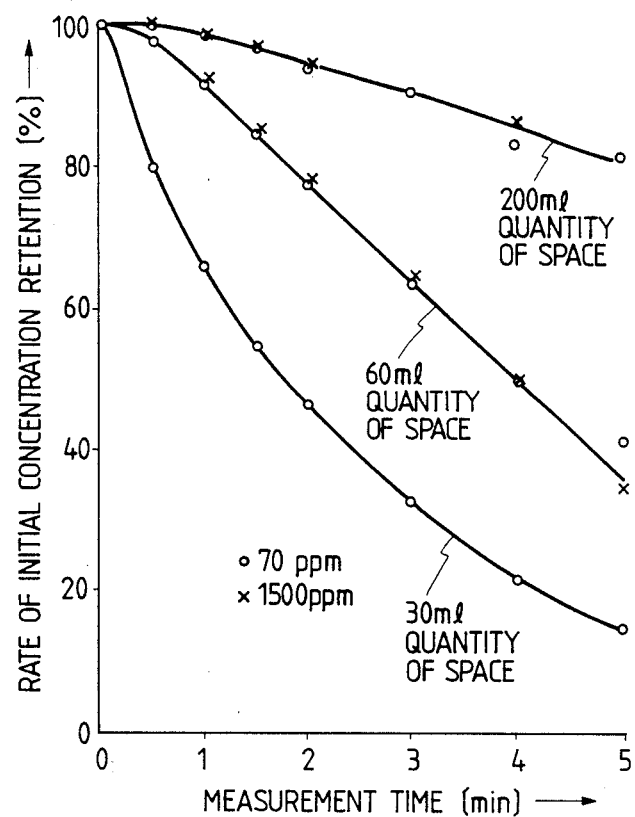
FIG. 7 is a diagram of a characteristic curve showing a rate of change of concentration with respect to extracting time in the third embodiment.
Figure 8:
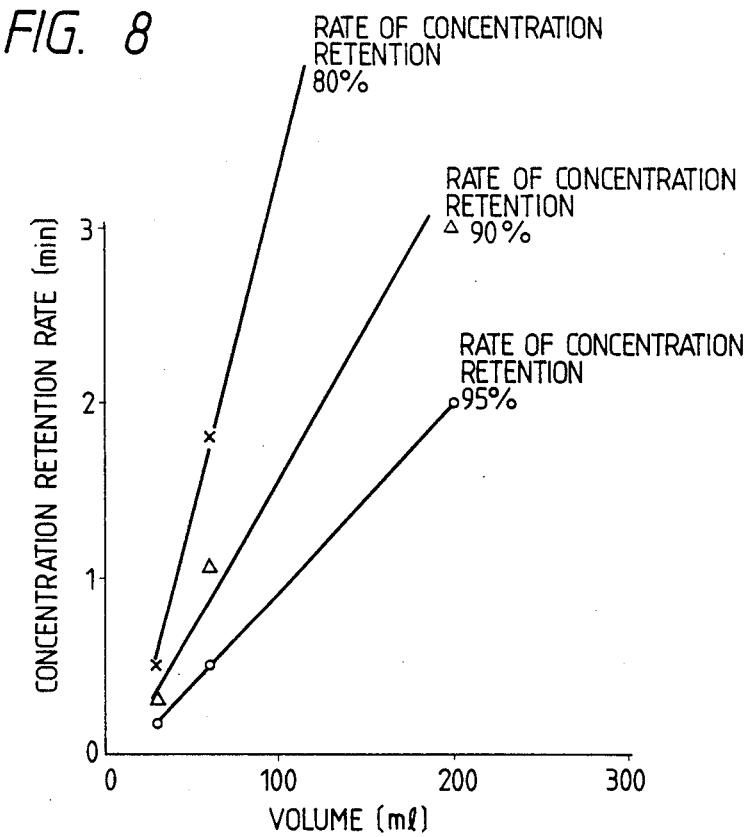
FIG. 8 is a diagram of a characteristic curve showing the guaranteeing time with respect to the quantity of space in the third embodiment.

Referring to FIGS. 3, 7 and 8, the third embodiment of the present invention will be described. The apparatus of this embodiment is the same as that of FIG. 3 which has been described with respect to the second embodiment.

In this apparatus, as already described, a semiconductor sensor composed of a suitable metal oxide such as $SnO_2$, $ZnO$, or the like, is used as the gas sensor 106.

Although a gas sensor of the kind described above is generally used in the condition that there is no limit on the measurement volume, it is indispensable to make the measurement volume constant in the foregoing analysis of a gas dissolved in oil. In order to make the measurement volume constant, however, the volume is limited and therefore if a gas to be detected is consumed by the gas sensor, a negative measurement error is caused.

In order to minimize such a measurement error, therefore, the absolute quantity of a dissolved gas in oil may be increased. The quantity, however, is limited in the case where miniaturization of the measuring apparatus and reduction of the measuring time are considered.

The quantity of gas consumption by the gas sensor will be discussed. As is well known, a semiconductor gas sensor is constituted by an n-type semiconductor which acts on the basis of a principle that the semiconductor receives electron from a reduction gas, such as hydrogen or the like to thereby reduce its resistance value when it contacts the reducing gas. At this time, for example, the hydrogen combines with oxygen in the air to form water to be consumed after the hydrogen has given electrons to the gas sensor, so that the hydrogen concentration in a small quantity of atmosphere is reduced.

FIG. 7 shows a result of an experiment which was made to confirm the foregoing phenomenon. In the drawing, the term of "volume" means the volume of the measurement system. Specifically, the term of "volume" means the sum of the respective volumes in the gas extraction vessel 101, the sensor chamber 105, and the pipes.

As is apparent in FIG. 7, it has been found that the smaller the volume is, the more the hydrogen gas is consumed in a short time and the larger the measurement error becomes. Therefore, it is an important problem for an operator to determine the timing when an indicated value of the meter should be read properly after initiation of measurement.

When a dissolved gas in oil is extracted by means of the foregoing circulation bubbling, generally, it takes about 2 minutes for the extracting operation. It is therefore necessary in the extracting operation to reduce the consumption, by the gas sensor, of the gas to be measured to the extent that no problem results.

FIG. 8 shows the relation between the initial concentration retention time and the volume obtained from the result of FIG. 7.

From FIG. 8, it can be understood that in order to improve the rate of initial concentration retention, the volume of the system should be large. Also, with a short extraction time, it is necessary to make the volume large. For example, it is necessary to set the volume to 65 ml in the case where the extraction is performed with a rate of concentration retention of 80% in 2 minutes by using the hydrogen gas sensor of $SnO_2$ used in this embodiment.

Here, if the rate of concentration retention is reduced, for example, to 70% in carrying out the extraction, the accuracy in measurement is undesirably lowered. Examples of such undesirable accuracy reduction are shown as values of a variation factor (%) in the following table.

|  | Oil Temperature 0° C. | Oil Temperature 25° C. | Oil Temperature 80° C. |
| --- | --- | --- | --- |
| 80% Rentention rate | 20% | 10% | 20% |
| 70% Rentention rate | 35% | 25% | 35% |

$$\text{Variation Factor} = \frac{\text{Standard Deviation}}{\text{Mean Value}} \times 100(\%)$$

It is therefore necessary to make the rate of concentration retention not smaller than 80%.

Consequently, it is understood that if the volume is established so that the consumption by the gas sensor of the gas to be measured is not larger than 20% during the period of time required for gas extraction, the variation factor, which is an indicator of accuracy in measurement, can be kept within a range of ±20%.

As described above, this third embodiment has an excellent effect that the measurement can be carried out with high accuracy. The system is arranged so that in measurement of the concentration of a dissolved gas in oil while extracted gas is circulated, a volume in which concentration can be kept is obtained from the gas consumption by a gas sensor to be used and the gas extracting time and the concentration of the dissolved gas is measured with the thus obtained volume.

A fourth embodiment of the present invention will now be described. The fourth embodiment relates to a method of cleaning an apparatus for measuring a dissolved gas in oil.

In a measuring apparatus such as that used in the first, second and third embodiments, when measurement is to be carried out on a second different oil sample after completing measurement of a first oil sample, it is necessary to clean the inside of the apparatus prior to the succeeding measurement.

To this end, the cover of the extraction vessel is opened, the old oil sample is discharged from the extraction vessel, and air is passed into and discharged from the gas recovering vessel and pipes to clean the insides of the gas recovering vessel and the pipes.

In the circulation bubbling system according to the present invention, however, dissolved gas remains in the oil sample even after completion of measurement, and therefore the dissolved gas remains in an extraction vessel even after complete discharge of the oil sample from the extraction vessel.

Accordingly, in the foregoing cleaning method, a plus error is sometimes caused if oil having a low concentration of gas is measured after measuring oil having a high concentration of gas.

It is therefore an object of this embodiment to make it possible to perform such cleaning in a short time with no influence on the succeeding measurement.

This embodiment has the following feature. A pipe connecting an extraction vessel to a gas recovering vessel is partially opened, while leaving the preceding measured oil sample in the state as contained in the extraction vessel, and air is passed from the opened portion of the pipe and discharged after being passed once through the extraction vessel. This operation is repeated before the gas concentration inside the extraction vessel, the gas recovering vessel, and the pipes becomes substantially equal to that of the gas concentration. Then, after the old oil sample has been discharged from the extraction vessel, the measurement is performed on the succeeding oil sample.

If air is repeatedly circulated while leaving the old measured oil sample in the state as contained in the extraction vessel, all the dissolved gas remaining not only in the insides of the extraction vessel, the gas recovering vessel, and the pipes, but in the oil sample is discharged to the outside.

The oil sample is discharged thereafter. It is apparent that no dissolved gas remains even after the discharge. Even if the succeeding oil sample is poured into the extraction vessel and measured, therefore, the measurement is not affected by the concentration of the preceding oil sample.

Figure 9:
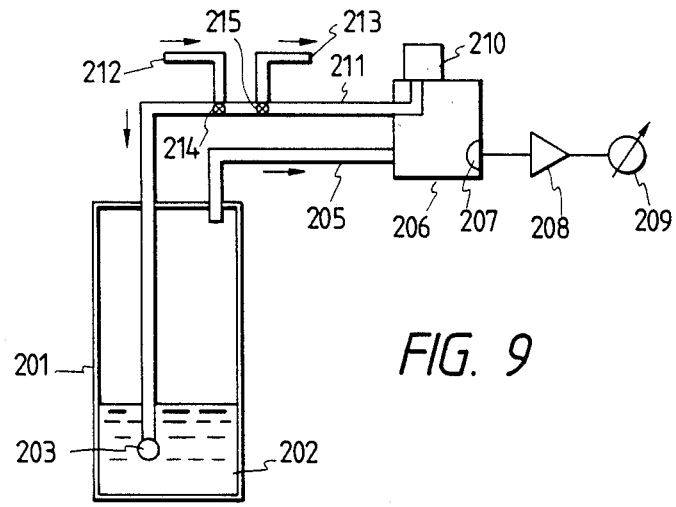
FIG. 9 is a diagram showing an arrangement for realizing the method of a fourth embodiment of the present invention.

Referring to FIG. 9, the fourth embodiment will be described more in further detail. FIG. 9 shows an apparatus for detecting a gas dissolved in oil, arranged substantially in the same manner as that of FIG. 3, in which the cleaning method of this embodiment is realized. Oil sample 202 is contained in an extraction vessel 201. A bubble generator 203 constituted by a ball filter, a bubble generation pipe, or the like, is disposed inside the extraction vessel 201. In measurement, the extraction vessel 201 is closed, and a bubbling gas such as air or the like is passed from an outside source into the bubble generator 203 through a pump 210.

Bubbles are generated with the air. The bubbles entrain gas dissolved in the oil sample 202. Gas extracted from the bubbles is sent to a gas recovering vessel 206 through a pipe 205 so as to be detected by a gas sensor 207.

The detected value is converted into an electric signal, and amplified by an amplifier 208. The detected value is indicated by a meter 209. A semiconductor sensor composed of metal oxide such as $SnO_2$, ZnO, or the like is used as the gas sensor.

The extracted gas in the gas recovering vessel 206 is returned to the extraction vessel 201 by the pump 210 through the pipe 211. Thus, the extracted gas is repeatedly circulated and the gas concentration is measured by circulation of the extracted gas.

Upon completion of the first measurement dissolved gas in the oil sample, cleaning is performed prior to initiation of the succeeding measurement. In this embodiment, first, the pipe 211 is partially opened so as to make a suction inlet 212 and a discharge outlet 213 communicate each other while leaving the preceding oil sample as it is kept in the extraction vessel 201.

Specifically, change-over valves 214 and 215 are provided in the pipe 211, so that the suction inlet 212 and the discharge outlet 213 are selectively connected to the pipe 211 by changing over the change-over valves 214 and 215.

Outside fresh air is sucked into the pipe 211 through the suction inlet 212, and sent into the extraction vessel 201. The air thus sent into the extraction vessel 201 is circulated from the extraction vessel 201 through the pipe 205, the gas recovering vessel 206, and the pipe 211, and discharged to the outside through the discharge outlet 213. The circulation of air is performed repeatedly for the necessary time.

When the gas concentration inside the respective portions becomes substantially equal to the external gas concentration, the change-over valves 214 and 215 are returned to their original states so that the suction inlet 212 and the discharge outlet 213 are disconnected from the pipe 211, and the pipes 205 and 211 are removed from the extraction vessel 201 so that the oil sample in the extraction vessel 201 is discharged. Thereafter, the succeeding oil sample to be measured is poured into the extraction vessel 201, and the same measurement as described above is performed.

If the foregoing cleaning is performed, almost all the dissolved gas remaining in the oil sample existing in the extraction vessel 201 is replaced by the fresh outside air. Even if the succeeding oil sample is poured into the extraction vessel 201 after discharge of the preceding oil sample, the succeeding measurement can be performed substantially without being affected by the gas concentration of the preceding oil sample.

Next, there will be described an experiment which was made by the present inventor.

The experiment was carried out under the conditions that 33 ml of an oil sample containing dissolved hydrogen gas was poured into the extraction vessel 201, the rate of air passed into and discharged through the suction inlet 212 and the discharge outlet 213, respectively, was set to 1 l/min, and the cleaning time was set to 2 minutes.

First, measurement was performed on an oil sample having a gas concentration of 5,000 ppm (first measurement). Then measurement was performed on an oil sample having a gas concentration of 0 ppm after the foregoing cleaning was carried out (second measurement). Then measurement was performed on an oil sample having a gas concentration of 500 ppm after the foregoing cleaning was carried out (third measurement), and finally measurement was performed on an oil sample having a gas concentration of 0 ppm after the foregoing cleaning was carried out (fourth measurement).

The following table shows the indicated values of the meter in the foregoing four measurements. Further, in order to make a comparison, the table also shows the results of measurement carried out under the same conditions by use of the same oil samples as those of the foregoing measurements according to the invention, in the case where cleaning was made by leading/discharging air into/from portions other than the extraction vessel (comparative example A), and in the case where cleaning was made by leading/discharging air into/from portions including the extraction vessel (comparative example B). All the concentration values are expressed as ppm.

|  | First Measurement | Second Measurement | Third Measurement | Fourth Measurement |
| --- | --- | --- | --- | --- |
| Example | 4800 | 5 or less | 500 | 0 |
| Comparative Example A | 4800 | 450 | 530 | 32 |
| Comparative Example B | 4800 | 40 | 500 | 15 |

As can be understood from the foregoing results, it is found that in each of the comparative examples A and B, each of the second third and fourth measurements was affected by the preceding measurement so that a value of gas concentration higher than the actual value of gas concentration was indicated by the meter. In the example according to the present invention, however, it was found that the influence was slight after a preceding measurement of high concentration and the influence was also slight after a preceding measurement of low concentration.

As described above in detail, this embodiment has an excellent effect in that it is possible to perform cleaning in a short time. Further, measurement can be performed without being affected by the concentration of the preceding oil sample even when the concentration of a gas dissolved in oil is repeatedly measured.

Having described preferred embodiments of the present invention, variations and modifications falling within the spirit of the invention may become apparent to those skilled in the art, and the scope of the present invention is to be defined only by the appended claims and their equivalents.

What is claimed is:

1. A method of measuring a dissolved gas in oil comprising the steps of:
   passing a bubbling gas into an oil sample having a dissolved gas in solution, taken out from oil handling equipment and contained in an extraction vessel, to form bubbles in said oil sample having a size within the range of from 0.1 to 8 mm;
   stripping dissolved gas from said oil sample with said bubbles to form bubbles containing a gas mixture of said bubbling gas and dissolved gas stripped from said oil sample;
   recovering the gas mixture in a gas recovering vessel and measuring the concentration of said dissolved gas with a gas sensor; and
   returning said recovered gas mixture into said extraction vessel through a pump to thereby circulate said recovered gas mixture.

2. The method of claim 1, wherein the combined volumes of said extraction vessel, said recovering vessel and connecting conduits are selected so that the volume of said dissolved gas consumed by said sensor during said stripping step is not larger than 20% of said combined volumes.

3. An apparatus for measuring a dissolved gas in oil comprising:
   an extraction vessel for containing an oil sample having a dissolved gas in solution;
   a circulating pump connected to said extraction vessel for blowing a stripping gas into said oil sample in said extraction vessel;
   a bubble generator connected to said pump for generating bubbles with said stripping gas blown by said pump and passing the bubbles through said oil sample to extract said dissolved gas, said bubble generator being adopted to provide bubbles having a size within the range of from 0.1 to 8 mm;
   a gas recovering vessel connected to said extraction vessel for recovering a mixture of said stripping gas bubbled through said oil sample and extracted dissolved gas, said gas recovering vessel having a gas sensor therein for measuring said dissolved gas in said mixture; and
   conduit means connecting said recovering vessel to said pump and for passing said recovered gas mixture in said gas recovering vessel into said extraction vessel so as to circulate said recovered gas mixture to said extraction vessel.

4. An apparatus for measuring a dissolved gas in oil comprising:
   a gas extraction vessel for containing an oil sample containing a dissolved gas;
   a circulating pump connected to said extraction vessel for blowing a stripping gas into said oil sample in said gas extraction vessel;
   a bubble generator connected to said pump for generating bubbles of stripping gas in said oil sample in said gas extraction vessel and passing said bubbles through said sample to extract said dissolved gas;
   a sensor chamber connected to said extraction vessel for recovering a mixture of said gas bubbled through said oil sample and extracted dissolved gas, said sensor chamber having a gas sensor therein for detecting and measuring said extracted dissolved gas in said mixture;
   conduit means for connecting said extraction vessel, said sensor chamber and said pump and for passing said recovered gas mixture in said sensor chamber into said extraction vessel so as to circulate said recovered gas mixture, wherein the combined volumes of said extraction vessel, said sensor chamber and said conduit means are such that the quantity of the dissolved gas to be measured which is consumed by said gas sensor during the time taken for said gas extraction is not larger than 20% of said combined volumes.

5. The apparatus of claim 3, wherein said oil sample has a volume less than the volume of said extraction vessel and an open space volume is provided in said extraction vessel above the level of said oil sample, the ratio of the volume of said sample to said open space volume being in the range of from 1:1 to 1:15.

6. The apparatus of claim 4, wherein said bubble generator is adapted to provide bubbles having a size within the range of from 0.1 to 8 mm.

7. The apparatus of claim 6, wherein said oil sample has a volume less than the volume of said extraction vessel and an open space volume is provided in said extraction vessel above the level of said oil sample, the ratio of the volume of said sample to said open space volume being in the range of from 1:1 to 1:15.

* * * * *